(12) United States Patent
Kogami et al.

(10) Patent No.: US 7,759,501 B2
(45) Date of Patent: Jul. 20, 2010

(54) PROCESS FOR PRODUCING N-MONOALKYL-3-HYDROXY-3-(2-THIENYL) PROPANAMINE AND INTERMEDIATE

(75) Inventors: Kenji Kogami, Kako-gun (JP); Noriyuki Hayashizaka, Kako-gun (JP); Syuzo Satake, Kako-gun (JP); Ichiro Fuseya, Kako-gun (JP); Hirokazu Kagano, Kako-gun (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 177 days.

(21) Appl. No.: 10/523,287

(22) PCT Filed: Jul. 15, 2003

(86) PCT No.: PCT/JP03/08950
§ 371 (c)(1), (2), (4) Date: Feb. 3, 2005

(87) PCT Pub. No.: WO2004/016603
PCT Pub. Date: Feb. 26, 2004

(65) Prior Publication Data
US 2005/0240030 A1 Oct. 27, 2005

(30) Foreign Application Priority Data
Aug. 6, 2002 (JP) ............................. 2002-229204

(51) Int. Cl.
*C07D 333/20* (2006.01)
*C07D 333/22* (2006.01)
(52) U.S. Cl. .......................................... 549/75; 549/72
(58) Field of Classification Search ................... 549/72, 549/74, 75
See application file for complete search history.

(56) References Cited

U.S. PATENT DOCUMENTS

| | | | | |
|---|---|---|---|---|
| 5,362,886 A | * | 11/1994 | Berglund | 549/75 |
| 5,491,243 A | * | 2/1996 | Berglund | 549/75 |
| 5,543,520 A | * | 8/1996 | Zimmermann | 544/331 |
| 5,939,436 A | * | 8/1999 | Carling et al. | 514/326 |
| 6,846,957 B2 | * | 1/2005 | Zelenin | 564/343 |
| 6,984,738 B2 | * | 1/2006 | Yokozawa et al. | 549/75 |
| 2004/0102651 A1 | * | 5/2004 | Zelenin | 564/343 |

FOREIGN PATENT DOCUMENTS

| EP | 0 372 470 A2 | 6/1990 |
|---|---|---|
| EP | 0 650 965 A1 | 5/1995 |
| JP | 60-246348 A | 12/1985 |
| JP | 02-202865 A | 8/1990 |
| JP | 07-188065 A | 7/1995 |

OTHER PUBLICATIONS

Cassella Farbwerke et al, CA 88: 105153, 1978.*
Singh et al, CA 115: 29157, 1991.*
Bogdanowicz-Szwed et al, CA136: 118356, 2001.*
Wright et al. (Journal of Medicinal Chemistry (1992), 35(22), 4061-8).*
CASREACT abstract # 122:132250 of Guseinov et al. (Zhurnal Organicheskoi Khimii (1994), 30(4), 496-9).*
Makarova et al. (Russian Journal of General Chemistry, vol. 71, No. 7, 2001, pp. 1126-1129.).*
Gribble et al. (Org. Prep. Proc. Int. v. 17, p. 317-384 (1985)).*
Smith and March (March's Advanced Organic Chemistry, 5th ed. (2001), Wiley, p. 2083), chapters 15 and 16 provided.*
Makarova et al. (Russian Journal of General Chemistry, vol. 37, No. 8, 2001, pp. 1099-1101.).*
Deeter et al. (Tetrahedron Lett., V. 31, No. 49, pp. 7101-7104 (1990)).*
Bartoli et al. (J. Chem. Soc. Perkin Trans. I, 537-543 (1994)).*
Nutaitis and Bernardo, Regioselective 1,2-reduction of conjugated enones and enals with sodium monoacetoxyborohydride: preparation of allylic alcohols, J. Org. Chem., 1989, 54 (23), 5629-5630.*
Johnson and Rickborn, Sodium borohydride reduction of conjugated aldehydes and ketones, J. Org. Chem., 1970, 35 (4), 1041-1045.*
Andrews and Mosbo, Syntheses of .beta.-diamines and .beta.-amino alcohols from .alpha.,.beta.-unsaturated ketones and aldehyde, methylamine, and borohydride reducing agents, J. Org. Chem., 1977, 42 (4), 650-652.*

(Continued)

*Primary Examiner*—Robert Havlin
(74) *Attorney, Agent, or Firm*—Knobbe, Martens, Olson & Bear LLP

(57) ABSTRACT

The present invention provides a process for producing an N-monoalkyl-3-hydroxy-3-(2-thienyl)propanamine represented by General Formula (2):

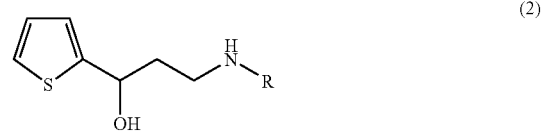

(2)

wherein R is $C_{1-4}$ alkyl, comprising the step of reducing (Z)-N-monoalkyl-3-oxo-3-(2-thienyl)propenamine represented by General Formula (1):

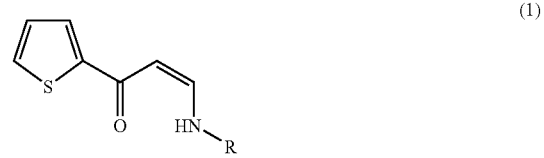

(1)

wherein R is as defined above. According to the present invention, an N-monoalkyl-3-hydroxy-3-(2-thienyl)propanamine which is for use as an intermediate for various pharmaceuticals can be produced in an industrially inexpensive and easy manner.

12 Claims, No Drawings

OTHER PUBLICATIONS

Huiling Liu, et al., "Chemo-Enzymatic Synthesis of the Antidepressant Duloxetine and Its Enantiomer," Chirality, 12, pp. 26-29, 2000.

Chatterjee et al., "Reaction of enaminones with thiacumulenes," *Phosphorus, Sulfur, and Silicon and the Related Elements* (1998) 133(1):251-266.

* cited by examiner

PROCESS FOR PRODUCING N-MONOALKYL-3-HYDROXY-3-(2-THIENYL) PROPANAMINE AND INTERMEDIATE

This application is the U.S. National Phase under 35 U.S.C. §371 of International Application PCT/JP2003/008950, filed on Jul. 15, 2003, which claims priority of Japanese Patent Application No. 2002-229204, filed on Aug. 6, 2002. The International Application was published under PCT Article 21(2) in a language other than English.

TECHNICAL FIELD

The present invention relates to a process for producing an N-monoalkyl-3-hydroxy-3-(2-thienyl)propanamine. N-monoalkyl-3-hydroxy-3-(2-thienyl)propanamines are highly reactive and useful as intermediates for various pharmaceuticals. The present invention relates also to a novel compound for use as a production intermediate of an N-monoalkyl-3-hydroxy-3-(2-thienyl)propanamine, i.e., a (Z)—N-monoalkyl-3-oxo-3-(2-thienyl)propenamine, and a production process thereof.

BACKGROUND ART

An example of a method known for producing an N-monoalkyl-3-hydroxy-3-(2-thienyl)propanamine is reducing 1-(2-thienyl)-3-chloropropane-1-one with sodium borohydride in ethanol to give 3-chloro-1-(2-thienyl)-1-propanol, halogen-exchanging this 3-chloro-1-(2-thienyl)-1-propanol with sodium iodide in acetone to give 3-iodo-1-(2-thienyl)-1-propanol, and reacting this 3-iodo-1-(2-thienyl)-1-propanol with an aqueous monomethylamine solution in tetrahydrofuran (CHIRALITY, 12, 26-29 (2000)). This method is not industrially advantageous since the starting material, i.e., 1-(2-thienyl)-3-chloropropane-1-one, is a highly unstable compound.

An example of a method known for producing N,N-dimethyl-3-hydroxy-3-(2-thienyl)propanamine is reacting 2-acetylthiophene with a dimethylamine hydrochloride in isopropanol in the presence of paraformaldehyde and hydrochloric acid to give 2-thienyl 2-dimethylaminoethyl ketone, and reducing this ketone with sodium borohydride in ethanol (Japanese Unexamined Patent Publication No. 1995-188065).

When an N-monoalkyl-3-hydroxy-3-(2-thienyl)propanamine is produced according to the method described immediately above using a monoalkylamine hydrochloride in place of a dimethylamine hydrochloride, it is problematic in that a dimeric N,N',N"-alkyl-bis[1-[3-oxo-3-(2-thienyl)propane]]amine is generated due to the unstable production intermediate, i.e., 2-thienyl 2-monoalkylaminoethyl ketone, which results in a low yield of N-monoalkyl-3-hydroxy-3-(2-thienyl)propanamine obtained after the reduction with sodium borohydride.

DISCLOSURE OF THE INVENTION

An object of the present invention is to provide a process for producing an N-monoalkyl-3-hydroxy-3-(2-thienyl)propanamine in an industrially inexpensive and easy manner, and a production intermediate thereof.

Other objects and characteristics of the present invention will become evident by the disclosure provided hereinbelow.

The inventors conducted extensive research to attain the objectives described above and found that a novel compound, i.e., a (Z)—N-monoalkyl-3-oxo-3-(2-thienyl)propenamine, is useful as a starting material for producing an N-monoalkyl-3-hydroxy-3-(2-thienyl)propanamine. They found also that, by reducing this novel compound, an N-monoalkyl-3-hydroxy-3-(2-thienyl)propanamine can be produced in an industrially inexpensive and easy manner and that this (Z)—N-monoalkyl-3-oxo-3-(2-thienyl)propenamine can be produced by reacting an alkali metal salt of β-oxo-β-(2-thienyl)propanal with a monoalkylamine compound. The inventors accomplished the present invention based on these findings.

In other words, the present invention provides processes for producing an N-monoalkyl-3-hydroxy-3-(2-thienyl)propanamine, a production intermediate of this compound, i.e., a (Z)—N-monoalkyl-3-oxo-3-(2-thienyl)propenamine, and production processes thereof as described below:

1. A process for producing an N-monoalkyl-3-hydroxy-3-(2-thienyl)propanamine represented by General Formula (2):

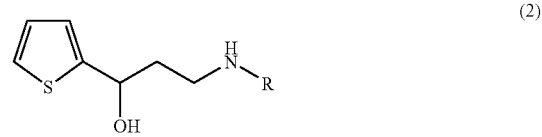

wherein R is $C_{1-4}$ alkyl, comprising the step of reducing a (Z)—N-monoalkyl-3-oxo-3-(2-thienyl)propenamine represented by General Formula (1):

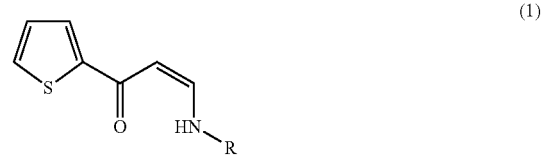

wherein R is as defined above.

2. The process according to Item 1, wherein the (Z)—N-monoalkyl-3-oxo-3-(2-thienyl)propenamine is reduced using sodium borohydride or sodium cyanoborohydride.

3. The process according to Item 1 or 2, wherein the (Z)—N-monoalkyl-3-oxo-3-(2-thienyl)propenamine is reduced in the presence of a proton-donating compound.

4. A (Z)—N-monoalkyl-3-oxo-3-(2-thienyl)propenamine represented by General Formula (1):

wherein R is $C_{1-4}$ alkyl.

5. The (Z)—N-monoalkyl-3-oxo-3-(2-thienyl)propenamine according to Item 4, wherein R in General Formula (1) is methyl.

6. A process for producing a (Z)—N-monoalkyl-3-oxo-3-(2-thienyl)propenamine represented by General Formula (1):

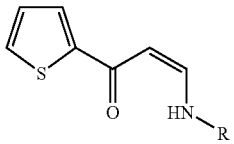

(1)

wherein R is $C_{1-4}$ alkyl, comprising the step of reacting an alkali metal salt of β-oxo-β-(2-thienyl)propanal represented by General Formula (3):

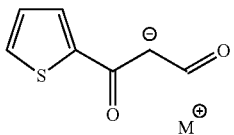

(3)

wherein M is an alkali metal atom, with a monoalkylamine compound represented by General Formula (4):

 (4)

wherein R is as defined above.

7. A process for producing an N-monoalkyl-3-hydroxy-3-(2-thienyl)propanamine represented by General Formula (2):

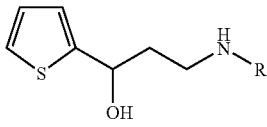

(2)

wherein R is $C_{1-4}$ alkyl, comprising the steps of:

reacting an alkali metal salt of β-oxo-β-(2-thienyl)propanal represented by General Formula (3):

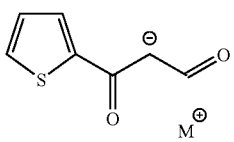

(3)

wherein M is an alkali metal atom, with a monoalkylamine compound represented by General Formula (4):

 (4)

wherein R is as defined above, to give a (Z)—N-monoalkyl-3-oxo-3-(2-thienyl)propenamine represented by General Formula (1):

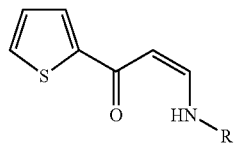

(1)

wherein R is as defined above; and reducing the (Z)—N-monoalkyl-3-oxo-3-(2-thienyl)propenamine.

8. The process according to Item 7, wherein the (Z)—N-monoalkyl-3-oxo-3-(2-thienyl)propenamine is reduced using sodium borohydride or sodium cyanoborohydride.

9. The process according to Item 7 or 8, wherein the (Z)—N-monoalkyl-3-oxo-3-(2-thienyl)propenamine is reduced in the presence of a proton-donating compound.

Hereinbelow, the process for producing an N-monoalkyl-3-hydroxy-3-(2-thienyl)propanamine, the production intermediate of this compound, i.e., a (Z)—N-monoalkyl-3-oxo-3-(2-thienyl)propenamine, and the production process thereof are described in more detail.

[Production of N-monoalkyl-3-hydroxy-3-(2-thienyl)propanamine]

The method for producing an N-monoalkyl-3-hydroxy-3-(2-thienyl)propanamine comprises the step of reducing a (Z)—N-monoalkyl-3-oxo-3-(2-thienyl)propenamine represented by General Formula (1):

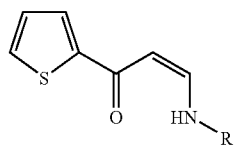

(1)

wherein R is $C_{1-4}$ alkyl.

Examples of $C_{1-4}$ alkyl are methyl, ethyl, n-propyl, isopropyl, n-butyl, t-butyl, etc.

Examples of reducing agents usable for the reduction are diisobutylaluminum hydride and like metal hydrides; sodium borohydride, sodium cyanoborohydride, lithium borohydride, potassium borohydride, and like complex metal hydrides; borane, 9-borabicyclo[3,3,1]nonane, and like borane compounds; hydrogen; etc. Among such reducing agents, complex metal hydrides are preferable because of their high reducing power, with sodium borohydride and sodium cyanoborohydride being particularly preferable.

The amount of reducing agent is preferably 0.1 to 7 mol, and more preferably 0.2 to 5 mol, per mol of (Z)—N-monoalkyl-3-oxo-3-(2-thienyl)propenamine. Amounts of reducing agent less than 0.1 molar equivalents are likely to result in an impaired yield because the reaction does not proceed sufficiently. On the other hand, amounts of reducing agent exceeding 7 mol do not exert effects justifiable for such amounts, and are therefore not economical.

Examples of reaction solvents usable in the reduction of the (Z)—N-monoalkyl-3-oxo-3-(2-thienyl)propenamine are pentane, hexane, cyclohexane, heptane, and like aliphatic hydrocarbons; benzene, toluene, xylene, chlorobenzene, and like aromatic hydrocarbons; diethyl ether, tetrahydrofuran, dioxane, and like ethers; methanol, ethanol, and like alcohols;

methyl acetate, ethyl acetate, butyl acetate, and like esters; etc. Among such reaction solvents, aromatic hydrocarbons are preferable, and toluene is particularly preferable.

The amount of reaction solvent is preferably 0.1 to 30 times, and more preferably 0.5 to 20 times, the weight of (Z)—N-monoalkyl-3-oxo-3-(2-thienyl)propenamine. Amounts of reaction solvent less than 0.1 times are likely to make stirring difficult. On the other hand, amounts of reaction solvent exceeding 30 times are likely to impair volume efficiency.

The reduction of the (Z)—N-monoalkyl-3-oxo-3-(2-thienyl)propenamine is preferably carried out in the presence of a proton-donating compound for the reduction reaction to proceed efficiently. Examples of proton-donating compounds are methanol, ethanol, and like alcohols; formic acid, acetic acid, monochloroacetic acid, dichloroacetic acid, trichloroacetic acid, and like carboxylic acids; hydrogen fluoride, hydrogen chloride, hydrogen bromide, hydrogen iodide, and like hydrogen halides; sulfuric acid; methylsulfuric acid, p-toluenesulfonic acid, and like sulfonic acids; etc. Among such examples, carboxylic acids are preferable, and acetic acid is particularly preferable, for the reduction reaction to readily progress.

The amount of proton-donating compound is preferably 20 mol or less, and more preferably 0.1 to 10 mol, per mol of (Z)—N-monoalkyl-3-oxo-3-(2-thienyl)propenamine. Amounts of proton-donating compound exceeding 20 molar equivalents do not exert effects justifiable for such amounts, and are therefore not economical.

The temperature for reducing the (Z)—N-monoalkyl-3-oxo-3-(2-thienyl)propenamine is preferably from 0° C. to 150° C., and more preferably from 20° C. to 100° C. Temperatures lower than 0° C. are likely to slow the reaction rate, thereby prolonging the reaction. On the other hand, temperatures exceeding 150° C. may result in impurity generation. Although the reaction time varies depending on the reaction temperature, it is preferably from 1 to 30 hours.

After the reaction, the reaction solution containing the N-monoalkyl-3-hydroxy-3-(2-thienyl)propanamine is phase-separated by adding water when a water-immiscible solvent is used as a reaction solvent. When a water-miscible solvent is used as a reaction solvent, water and a water-immiscible solvent, e.g., toluene, are added for phase separation. The solvent contained in the organic phase obtained by the phase separation is distilled off, and crystals thus precipitated are then recrystallized, thereby enabling the N-monoalkyl-3-hydroxy-3-(2-thienyl)propanamine to be isolated.

The N-monoalkyl-3-hydroxy-3-(2-thienyl)propanamine thus obtained is a compound represented by General Formula (2):

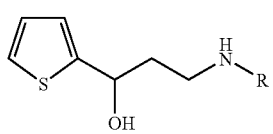

(2)

wherein R is $C_{1-4}$ alkyl.

Examples of $C_{1-4}$ alkyl are methyl, ethyl, n-propyl, isopropyl, n-butyl, t-butyl, etc.

Specific examples of N-monoalkyl-3-hydroxy-3-(2-thienyl)propanamines are N-monomethyl-3-hydroxy-3-(2-thienyl)propanamine, N-monoethyl-3-hydroxy-3-(2-thienyl)propanamine, N-mono(n-propyl)-3-hydroxy-3-(2-thienyl)propanamine, N-monoisopropyl-3-hydroxy-3-(2-thienyl)propanamine, N-mono(n-butyl)-3-hydroxy-3-(2-thienyl)propanamine, N-mono(t-butyl)-3-hydroxy-3-(2-thienyl)propanamine, etc.

Such N-monoalkyl-3-hydroxy-3-(2-thienyl)propanamines are highly reactive and useful as intermediates for various pharmaceuticals.

The (Z)—N-monoalkyl-3-oxo-3-(2-thienyl)propenamine represented by General Formula (1):

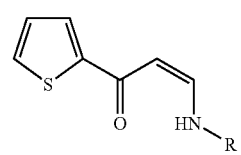

(1)

wherein R is $C_{1-4}$ alkyl, used in the process for producing an N-monoalkyl-3-hydroxy-3-(2-thienyl)propanamine of the invention is a novel compound.

Examples of $C_{1-4}$ alkyl are methyl, ethyl, n-propyl, isopropyl, n-butyl, t-butyl, etc.

Specific examples of (Z)—N-monoalkyl-3-oxo-3-(2-thienyl)propenamines are (Z)—N-monomethyl-3-oxo-3-(2-thienyl)propenamine, (Z)—N-monoethyl-3-oxo-3-(2-thienyl)propenamine, (Z)—N-mono(n-propyl)-3-oxo-3-(2-thienyl)propenamine, (Z)—N-monoisopropyl-3-oxo-3-(2-thienyl)propenamine, (Z)—N-mono(n-butyl)-3-oxo-3-(2-thienyl)propenamine, (Z)—N-mono(t-butyl)-3-oxo-3-(2-thienyl)propenamine, etc. Among such examples, (Z)—N-monomethyl-3-oxo-3-(2-thienyl)propenamine is preferable.

[Production of (Z)—N-monoalkyl-3-oxo-3-(2-thienyl)propenamine]

(Z)—N-monoalkyl-3-oxo-3-(2-thienyl)propenamines represented by General Formula (1) can be obtained by reacting an alkali metal salt of β-oxo-β-(2-thienyl)propanal represented by General Formula (3):

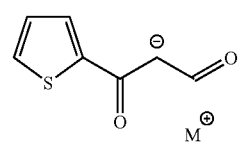

(3)

wherein M is an alkali metal atom, with a monoalkylamine compound represented by General Formula (4):

H$_2$N—R  (4)

wherein R is $C_{1-4}$ alkyl.

Alkali metal salts of β-oxo-β-(2-thienyl)propanal usable in the present invention are compounds represented by General Formula (3):

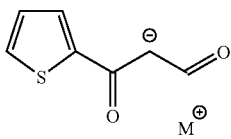

(3)

wherein M is an alkali metal atom.

Examples of alkali metal atoms are lithium, sodium, potassium, etc.

Specific examples of alkali metal salts of β-oxo-β-(2-thienyl)propanal are the lithium salt of β-oxo-β-(2-thienyl)propanal, the sodium salt of β-oxo-β-(2-thienyl)propanal, the potassium salt of β-oxo-β-(2-thienyl)propanal, etc. Among such examples, the sodium salt of β-oxo-β-(2-thienyl)propanal is preferable.

Methods for producing alkali metal salts of β-oxo-β-(2-thienyl)propanal usable in the present invention are not limited. An example thereof is to react 2-acetylthiophene with an alkali metal methoxide in ethyl formate (Japanese Unexamined Patent Publication No. 1990-202865).

Monoalkylamine compounds usable herein are compounds represented by General Formula (4):

H$_2$N—R  (4)

wherein R is C$_{1-4}$ alkyl.

Examples of C$_{1-4}$ alkyl are methyl, ethyl, n-propyl, isopropyl, n-butyl, t-butyl, etc.

Specific examples of monoalkylamine compounds are monomethylamine, monoethylamine, mono(n-propyl)amine, monoisopropylamine, mono(n-butyl)amine, mono(t-butyl)amine, etc. Among such examples, monomethylamine is preferable.

Hydrochloric acid salts and sulfuric acid salts of the aforementioned monoalkylamine compounds can be used as monoalkylamine compounds in the present invention.

The amount of monoalkylamine compound is preferably 1 to 5 mol, and more preferably 1 to 3 mol, per mol of alkali metal salt of β-oxo-β-(2-thienyl)propanal. Amounts of monoalkylamine compound less than 1 mol are likely to result in an impaired yield. On the other hand, amounts of monoalkylamine compound exceeding 5 mol do not exert effects justifiable for such amounts, and are therefore not economical.

Examples of reaction solvents usable in the reaction of the alkali metal salt of β-oxo-β-(2-thienyl)propanal and the monoalkylamine compound are pentane, hexane, cyclohexane, heptane, and like aliphatic hydrocarbons; benzene, toluene, xylene, chlorobenzene, and like aromatic hydrocarbons; diethyl ether, tetrahydrofuran, dioxane, and like ethers; methanol, ethanol, and like alcohols; methyl acetate, ethyl acetate, butyl acetate, and like esters; etc. Among such reaction solvents, alcohols are preferable, and methanol is particularly preferable.

The amount of reaction solvent is preferably 0.1 to 30 times, and more preferably 0.5 to 20 times, the weight of alkali metal salt of β-oxo-β-(2-thienyl)propanal. Amounts of reaction solvent less than 0.1 times are likely to make stirring difficult whereas amounts of reaction solvent exceeding 30 times are likely to impair volume efficiency.

The temperature for the reaction of the alkali metal salt of β-oxo-β-(2-thienyl)propanal with the monoalkylamine compound is preferably from 0° C. to 100° C., and more preferably from 10° C. to 80° C. Reaction temperatures lower than 0° C. are likely to slow the reaction rate, thereby prolonging the reaction. On the other hand, reaction temperatures exceeding 100° C. are likely to result in impurity generation. Although the reaction time varies depending on the reaction temperature, it is preferably from 1 to 30 hours.

After the reaction, the solvent is distilled off, and an aqueous sodium hydroxide solution and an organic solvent such as methyl t-butyl ether, toluene, or the like are added to the reaction solution for phase separation to obtain an organic phase. The solvent is distilled off from the thus-obtained organic phase, and the thus-precipitated crystals are washed and dried, thereby enabling the (Z)—N-monoalkyl-3-oxo-3-(2-thienyl)propenamine to be isolated.

Moreover, an N-monoalkyl-3-hydroxy-3-(2-thienyl)propanamine can be obtained without isolating the (Z)—N-monoalkyl-3-oxo-3-(2-thienyl)propenamine above by subjecting it to reduction.

The present invention provides a process for producing an N-monoalkyl-3-hydroxy-3-(2-thienyl)propanamine in an industrially inexpensive and easy manner, which is highly reactive and useful as an intermediate for various pharmaceuticals, and a production intermediate thereof.

BEST MODE FOR CARRYING OUT THE INVENTION

Examples are given below to illustrate the invention in more detail, but the scope of the invention is not limited to these examples.

EXAMPLE 1

88.1 g (0.50 mol) of the sodium salt of β-oxo-β-(2-thienyl)propanal and 168 g of methanol were introduced into a 1-liter 4-necked flask equipped with a stirrer, condenser, thermometer and dropping funnel. 87.8 g (0.50 mol) of a 38.5 wt. % aqueous monomethylamine hydrochloride solution was added dropwise at 25° C. over 20 minutes. After the dropwise addition, reaction was carried out at 30° C. for 5 hours.

After the reaction, methanol was distilled off, and 121.4 g of a 3.1 wt. % aqueous sodium hydroxide solution and 100 g of methyl t-butyl ether were added for phase separation. The solvent was distilled off from the organic phase thus separated, and the thus-precipitated crystals were filtered. The crystals thus obtained were washed twice with 100 g of ethanol and dried, thereby giving 62.5 g (0.374 mol) of (Z)—N-monomethyl-3-oxo-3-(2-thienyl)propenamine. The yield thereof based on the sodium salt of β-oxo-β-(2-thienyl)propanal was 74.8%.

The (Z)—N-monomethyl-3-oxo-3-(2-thienyl)propenamine thus obtained exhibited the following properties:

Molecular weight: 167.23

Melting point: 85.3° C. to 86.4° C.

Elemental analysis: C, 57.23%; H, 5.55%; N, 8.38% (theoretical value: C, 57.46%; H, 5.42%; N, 8.37%)

Infrared absorption spectrum (KBr, cm$^{-1}$): 3230, 3079, 3064, 2929, 2904, 2813, 1629, 1552, 1513, 1488, 1427, 1413, 1351, 1290, 1251, 1234, 1176, 1145, 1093, 1060, 1012, 979, 954, 856, 842, 759, 740, 698, 663, 565, 468, 453

$^1$H-NMR spectrum (CDCl$_3$, TMS standard) δ (ppm): 9.90 (b, 1H), 7.54 (dd, 1H), 7.45 (dd, 1H), 7.06 (dd, 1H), 6.85 (dd, 1H), 5.57 (d, 1H), 3.05 (d, 3H)

EXAMPLE 2

8.7 g (0.052 mol) of (Z)—N-monomethyl-3-oxo-3-(2-thienyl)propenamine as obtained in Example 1, 6.2 g (0.103 mol) of acetic acid, and 42 g of toluene were introduced into a 300 ml 4-necked flask equipped with a stirrer, condenser, thermometer and dropping funnel, and heated to 50° C. After adding 1.966 g (0.052 mol) of sodium borohydride, reaction was carried out at 80° C. for 2 hours.

After the reaction, the reaction solution was cooled to 25° C., and 30 g of a 12.5 wt. % aqueous sodium hydroxide solution was added thereto for phase separation. The solvent was distilled off from the organic phase thus separated, and the thus-precipitated crystals were filtered. The crystals thus obtained were recrystallized in a mixed solvent of toluene and heptane (weight ratio=1:3), thereby giving 6.5 g (0.039 mol) of N-monomethyl-3-hydroxy-3-(2-thienyl)propanamine. The yield thereof based on (Z)—N-monomethyl-3-oxo-3-(2-thienyl)propenamine was 75.0%.

EXAMPLE 3

88.1 g (0.50 mol) of the sodium salt of β-oxo-β-(2-thienyl) propanal and 168 g of methanol were introduced into a 1-liter 4-necked flask equipped with a stirrer, condenser, thermometer and dropping funnel. 87.8 g (0.50 mol) of a 38.5 wt. % aqueous monomethylamine hydrochloride solution was added dropwise at 25° C. over 20 minutes. After the dropwise addition, reaction was carried out at 30° C. for 5 hours.

After the reaction, methanol was distilled off, and 400 g of toluene was added for phase separation. The organic phase obtained by phase separation was returned to the flask, and water was distilled off at 110° C. Toluene that had been distilled off during distillation due to azeotropy with water was separated from the water and returned to the flask. The organic phase was cooled to 25° C., mixed with 60 g (1.0 mol) of acetic acid, and heated to 50° C. After adding 18.9 g (0.5 mol) of sodium borohydride, reaction was carried out at 80° C. for 2 hours.

After the reaction, the reaction solution was cooled to 25° C., and 290 g of a 12.5 wt. % aqueous sodium hydroxide solution was added thereto for phase separation. The solvent was distilled off from the organic phase thus separated, and the thus-precipitated crystals were filtered. The crystals thus obtained were recrystallized in a mixed solvent of toluene and heptane (weight ratio=1:3), thereby giving 61.6 g (0.36 mol) of N-monomethyl-3-hydroxy-3-(2-thienyl)propanamine. The yield thereof based on the sodium salt of β-oxo-β-(2-thienyl)propanal was 72.0%.

The invention claimed is:

1. A process for producing an N-monoalkyl-3-hydroxy-3-(2-thienyl)propanamine represented by General Formula (2):

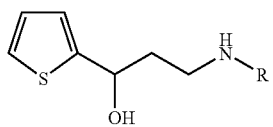
(2)

wherein R is $C_{1-4}$ alkyl, comprising the step of reducing a (Z)-N-monoalkyl-3-oxo-3-(2-thienyl)propenamine, in the presence of a carboxylic acid, represented by General Formula (1):

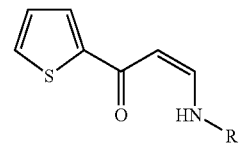
(1)

wherein R is as defined above.

2. The process according to claim 1, wherein the (Z)-N-monoalkyl-3-oxo-3-(2-thienyl)propenamine is reduced using sodium borohydride or sodium cyanoborohydride.

3. A (Z)-N-monoalkyl-3-oxo-3-(2-thienyl)propenamine represented by General Formula (1):

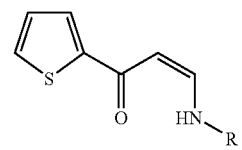
(1)

wherein R is $C_{1-4}$ alkyl.

4. The (Z)-N-monoalkyl-3-oxo-3-(2-thienyl)propenamine according to claim 3, wherein R in General Formula (1) is methyl.

5. A process for producing an N-monoalkyl-3-hydroxy-3-(2-thienyl)propanamine represented by General Formula (2):

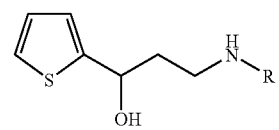
(2)

wherein R is $C_{1-4}$ alkyl, comprising the steps of:
reacting an alkali metal salt of β-oxo-β-(2-thienyl)propanal represented by General Formula (3):

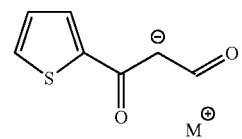
(3)

wherein M is an alkali metal atom, with a monoalkylamine compound represented by General Formula (4) or a hydrochloric acid salt or sulfuric acid salt thereof:

(4)

wherein R is as defined above, to give a (Z)-N-monoalkyl-3-oxo-3-(2-thienyl)propenamine represented by General Formula (1):

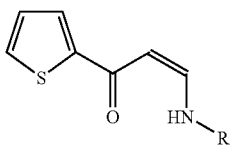 (1)

wherein R is as defined above; and reducing the (Z)-N-monoalkyl-3-oxo-3-(2-thienyl)propenamine, in the presence of a carboxylic acid.

6. The process according to claim 5, wherein the (Z)-N-monoalkyl-3-oxo-3-(2-thienyl)propenamine is reduced using sodium borohydride or sodium cyanoborohydride.

7. The process according to claim 1, wherein the reducing step of the process is conducted in a hydrocarbon solvent.

8. The process according to claim 7, wherein the hydrocarbon solvent is an aromatic hydrocarbon solvent.

9. The process according to claim 7, wherein the hydrocarbon solvent is selected from the group consisting of pentane, hexane, cyclohexane, heptane, benzene, toluene, and xylene.

10. The process according to claim 9, wherein the hydrocarbon solvent is toluene.

11. The process according to claim 7, wherein the monoalkylamine compound represented by General Formula (4):

$$H_2N-R \qquad (4)$$

is a hydrochloride salt or a sulfuric acid salt.

12. The process according to claim 11, wherein the monoalkylamine compound represented by General Formula (4):

$$H_2N-R \qquad (4)$$

is a hydrochloride salt.

* * * * *

UNITED STATES PATENT AND TRADEMARK OFFICE
CERTIFICATE OF CORRECTION

| | | |
|---|---|---|
| PATENT NO. | : 7,759,501 B2 | Page 1 of 1 |
| APPLICATION NO. | : 10/523287 | |
| DATED | : July 20, 2010 | |
| INVENTOR(S) | : Kenji Kogami et al. | |

It is certified that error appears in the above-identified patent and that said Letters Patent is hereby corrected as shown below:

At Column 12, Line 6, in Claim 11, please delete "claim 7" and insert --claim 5--, therefor.

Signed and Sealed this
Fifth Day of April, 2011

David J. Kappos
*Director of the United States Patent and Trademark Office*